United States Patent
Holmström et al.

(10) Patent No.: US 6,529,777 B1
(45) Date of Patent: Mar. 4, 2003

(54) ELECTRODE FOR TISSUE STIMULATION

(75) Inventors: Nils Holmström, Jarfälla (SE);
Sven-Erik Hedberg, Kungsängen (SE);
Kenth Nilsson, Åkersberg (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/622,817

(22) PCT Filed: Sep. 17, 1999

(86) PCT No.: PCT/SE99/00205
§ 371 (c)(1),
(2), (4) Date: Aug. 23, 2000

(87) PCT Pub. No.: WO99/41169
PCT Pub. Date: Aug. 26, 1999

(30) Foreign Application Priority Data

Feb. 23, 1998 (SE) .............................................. 9800520

(51) Int. Cl.⁷ ................................................. A61N 1/05
(52) U.S. Cl. ............................ 607/119; 607/3; 607/122; 607/9
(58) Field of Search ................................ 607/119, 116, 607/122–128, 1, 2, 3, 9, 17–26

(56) References Cited

U.S. PATENT DOCUMENTS

| | | | |
|---|---|---|---|
| 5,304,208 A | 4/1994 | Inguaggiato et al. | |
| 5,433,731 A | 7/1995 | Hoegnelid et al. | |
| 5,476,499 A | 12/1995 | Hirschberg | |
| 5,935,158 A | * 8/1999 | Holmstrom et al. ........ | 607/116 |

FOREIGN PATENT DOCUMENTS

| | | |
|---|---|---|
| EP | 0 515 319 | 11/1992 |
| EP | 0 924 935 | 2/1998 |
| WO | WO 95/27531 | 10/1995 |
| WO | WO 98/03134 | 1/1998 |

* cited by examiner

Primary Examiner—George R. Evanisko
(74) Attorney, Agent, or Firm—Schiff Hardin & Waite

(57) ABSTRACT

In an implantable electrode for an electrode lead for a stimulation device for stimulating tissue, the electrode is formed as a biocompatible piezoelectric electrode which is adapted to be in direct electrical contact with tissue for electrically and mechanically stimulating the tissue and for detecting electrical and mechanical evoked response of the stimulated tissue. The stimulation device can include circuitry for making a diagnosis of a heart condition using signals received from the implantable electrode.

16 Claims, 3 Drawing Sheets

ELECTRODE FOR TISSUE STIMULATION

BACKGROUND OF THE INVENTION

1. Field of the Invention

The invention relates generally to an electrode for implantable stimulation devices such as heart pacemakers or defibrillators. The invention relates further to implantable leads and stimulation devices such as heart pacemakers or defibrillators which employ such an electrode. Moreover, the invention relates to the use of the electrode for diagnosing the condition of stimulated tissue. In particular, the invention relates to an electrode which is adapted to electrically and mechanically transfer stimulation energy to tissue, to an electrode which is adapted to electrically and mechanically receive electrical and mechanical evoked response of the tissue to which stimulation energy has been transferred and to an electrode which is adapted for a combination of the two.

2. Description of the Prior Art

The life span of most pacemakers is dictated by the rate at which their batteries drain. Thus, a substantial effort has been directed toward minimizing the amount of energy used by pacemakers, while ensuring that the devices continue to deliver effective therapy. For example, demand pacemakers effectively reduce the battery drain by delivering pacing pulses only when required, i.e. if the pacemaker has not detected any spontaneous activity. Another way to reduce the current consumption is to minimize the amplitude and/or the duration of the stimulation pulse to a value just above the threshold. However, there are for example times when the heart emits an electrical signal, without providing a corresponding mechanical contraction (electromechanical dissociation). However, the pacemaker detects and interprets the electrical signal as an intrinsic beat or an evoked response. There are also times when the heart does not respond normally with increased cardiac output for increased stimulation rate as for example for patients with coronary artery disease during angina pectoris.

A way of minimizing the amount of energy needed for defibrillation, while ensuring that the defibrillators continue to deliver effective therapy, is disclosed in U.S. Pat. No. 5,433,731 a defibrillator having means for supplying the heart with a mechanical shock instead of an electrical shock. One embodiment discloses an electrode for supplying a defibrillation pulse, whereby the electrode is provided with an element on its distal exterior, which presses against the heart tissue and converts the electrical energy into mechanical energy. The element can for example be a piezoelectric element.

U.S. Pat. No. 5,304,208 discloses a cardiostimulator device having an electrode including an acceleration sensor for detecting the acceleration to which the cardiac mass is subjected as a reaction to any contraction whatsoever of the cardiac mass. The acceleration sensor is solely sensitive to inertial forces and can therefore be located in an entirely rigid capsule and consequently be entirely insensitive to the pressure in the ventricle or the atrium, and to pressure which the cardiac wall can exert, particularly on the distal electrode.

SUMMARY OF THE INVENTION

It is an object of the present invention to provide an implantable electrode, an electrode lead embodying an implantable electrode, and an implantable stimulation device employing an electrode lead, which avoid the aforementioned disadvantages of known leads and stimulators.

This object is inventively achieved in accordance with the principles of the present invention in an implantable electrode for an implantable stimulation device, the implantable electrode having a conductive core covered by a biocompatible piezoelectric material adapted to be in direct contact with tissue when implanted, and wherein the entire piezoelectric surface of the implantable electrode is adapted for electrically and mechanically transferring stimulation energy to the surrounding tissue, and/or is adapted to electrically and mechanically receive electrical and mechanical evoked or intrinsic responses of tissue, to which stimulation energy can be transferred.

The above object is also achieved in an electrode lead having an implantable electrode as described above, and further having a conductor for delivering stimulation energy to the piezoelectric material and/or for conducting signals from the piezoelectric material, the signals from the piezoelectric material representing the aforementioned electrical and mechanical evoked or intrinsic response of the tissue.

The above object is also achieved in an implantable stimulation device for stimulating tissue having an electrode lead with an implantable electrode as described above, and further having a stimulation pulse generator for delivering stimulation energy to the implantable electrode, and a detector for receiving signals from the implantable electrode corresponding to the aforementioned electrical and mechanical evoked or intrinsic response of the tissue.

An advantage of the invention is that it is possible to more reliably stimulate heart tissue and to detect a heart contraction. As a result a lower energy consumption is ensured.

According to the invention, the piezoelectric electrode is formed of a biocompatible piezoelectric material adapted to be in direct contact with the tissue, it surprisingly has been found that the conductive layer hitherto believed necessary can be excluded. In one embodiment the piezoelectric electrode is the tip electrode and in another embodiment the piezoelectric electrode is the ring electrode. In a preferred embodiment the stimulation pulse generator supplies the electrode with a chopped stimulation pulse.

DESCRIPTION OF THE PREFERRED EMBODIMENTS

Figure 1A:
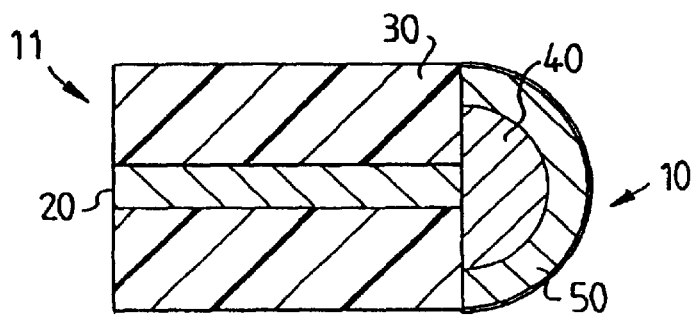
FIGS. 1A and 1B are respective schematic illustrations of two embodiments of a top electrode in accordance with the invention, for electrically and mechanically stimulating tissue and detecting an evoked response.
Figure 1B:
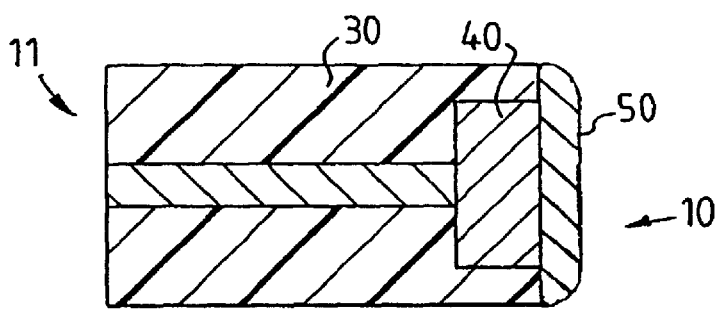
Figure 3:
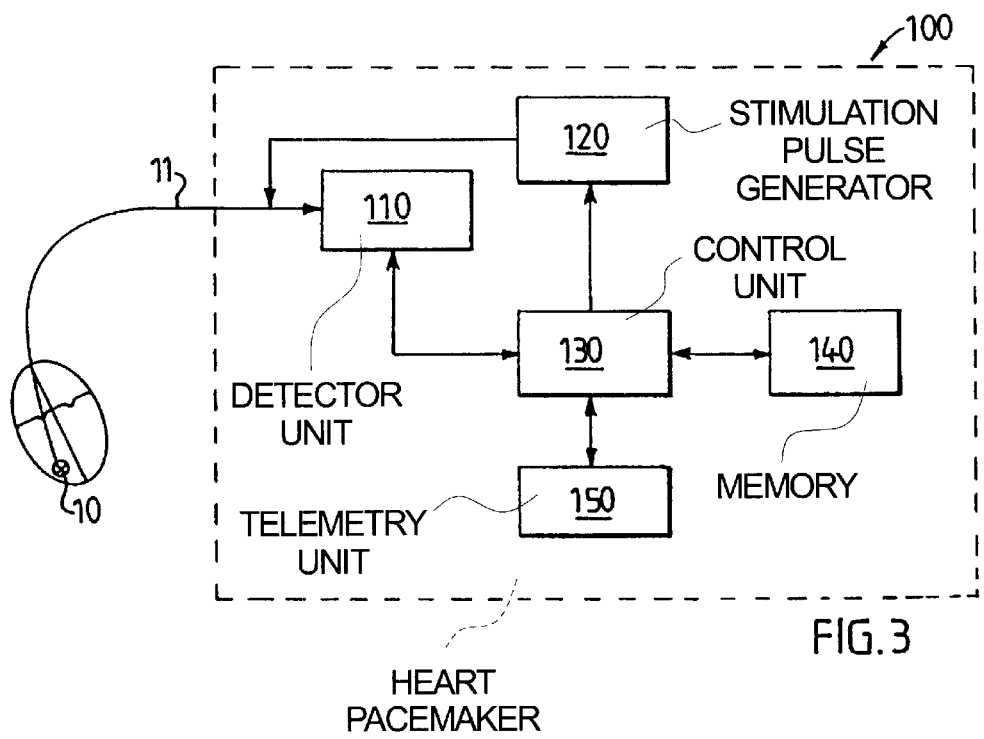
FIG. 3 is a schematic illustration of a cardiac pacemaker having an electrode in accordance with the invention.

FIGS. 1A and 1B, show an electrode 10 for a heart pacemaker 100 (see FIG. 3). The electrode 10 includes a conductor 20 enclosed by an insulator 30, e.g. silicon rubber. The conductor 20 is at one end in contact with an electrically conductive core 40, which is covered with a piezoelectric material 50. So as to obtain a high capacitance usually of the order 10–100 nF, the layer of piezoelectric material is very thin (0.1–5 $\mu$m). The piezoelectric material 50 is biocompatible. The metal core 40 and the piezoelectric layer 50, i.e. the piezoelectric electrode, form the tip of the electrode lead 11. FIGS. 1A and 1B show a hemispherical and a planar embodiment of the tip respectively, the planar embodiment being more sensitive to how it is placed with respect to the myocardial tissue. In a preferred embodiment the conductor 20 is made of the commonly used alloy MP35 and the conductive core 40 of e.g. graphite, titanium, platinum or iridium. The size of the electrode is about the same as for standard electrodes and may for instance vary between 1–10 mm$^2$.

It should be noted that the term biocompatible should be read as encompassing all materials that may be in direct contact with the tissue without adverse effects. Thus, the piezoelectric material PZT, a material that at least in some compositions contains lead and therefore sometimes is considered to be not biocompatible, possibly could be termed biocompatible when used in minute amounts. The amounts that would be used in the above preferred embodiment could be termed minute in view of the maximal amounts of lead that in the worst case could be released from the piezoelectric layer.

Figure 1C:
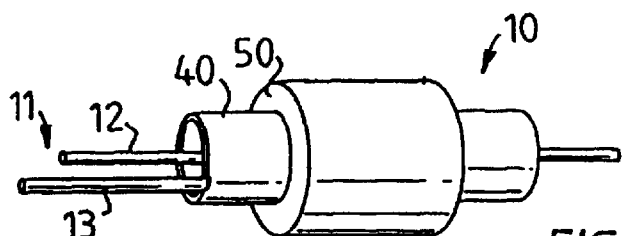
FIG. 1C is a schematic illustration of an embodiment of a ring electrode in accordance with the invention, for electrically and mechanically stimulating tissue and for detecting an evoked response.
Figure 1D:
FIG. 1D is a schematic illustration of an electrode lead in accordance with an embodiment of the invention.
Figure 4:
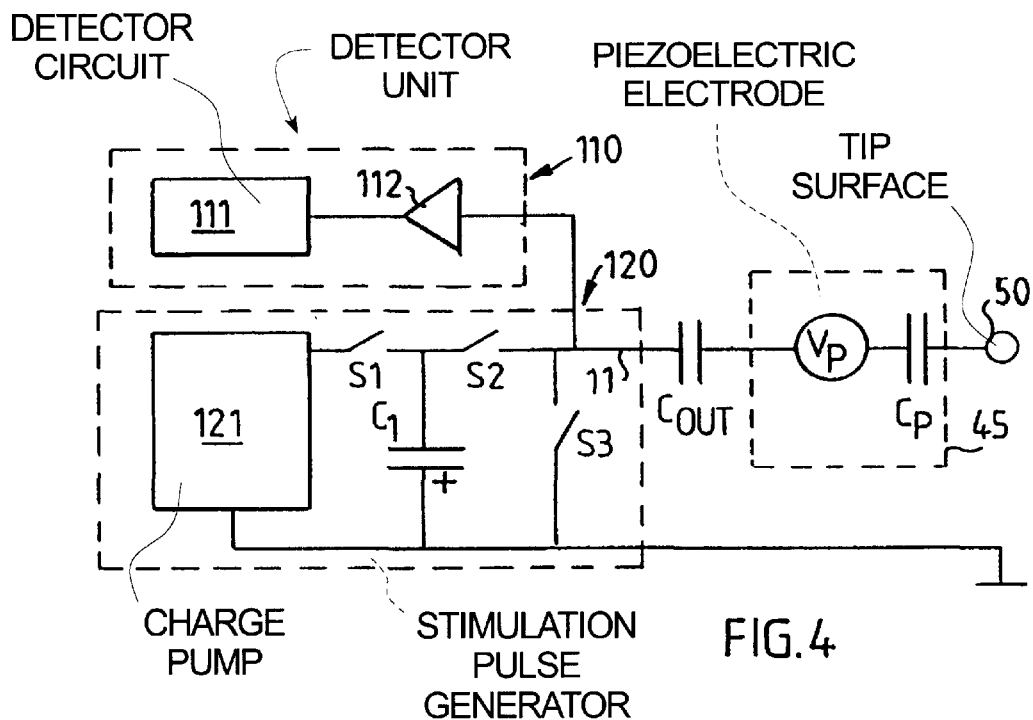
FIG. 4 is a schematic circuit diagram of a cardiac pacemaker in accordance with a first embodiment of the invention.
Figure 5:
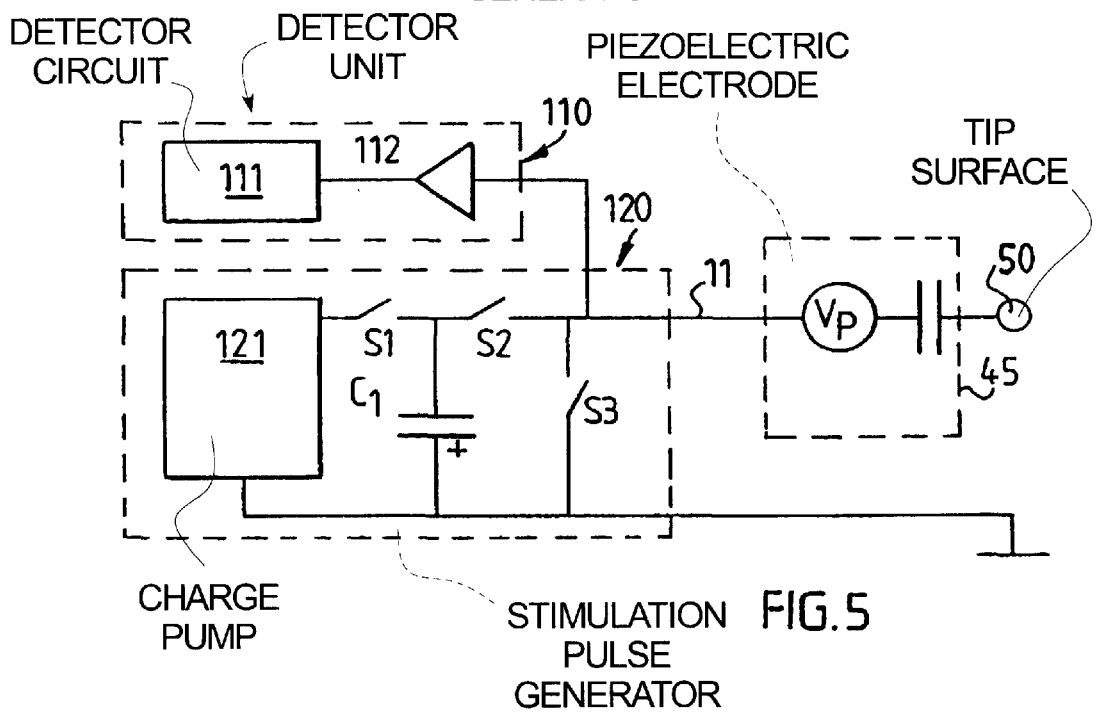
FIG. 5 is a schematic circuit diagram of a cardiac pacemaker in accordance with a further embodiment of the invention.

According to yet another embodiment of the invention, FIGS. 1C and 1D show a coaxial stimulating and sensing piezoelectric electrode 40, 50. The coaxial piezoelectric electrode 40, 50 is positioned about 1 to 15 cm behind the tip having an endocardial stimulation electrode 200. This embodiment may e.g. be used in a single lead DDD pacemaker system as disclosed in U.S. Pat. No. 5,476,499. The tip is thereby screwed into the atrial myocardium and a loop descends into the ventricle and makes contact with the ventricular wall. The design of the lead 11 is such that the ring 10 of the lead 11 is found in the contact area and the ring 10 comprises the coaxial piezoelectric electrode 40, 50. The lead 11 must have two conductors in this case. One conductor 12 is connected to the tip and atrial part of the DDD pacemaker. The other conductor 13 is connected to the piezoelectric electrode 40, 50 and the ventricular circuits of the pacemaker. The block schematics in FIGS. 3, 4 and 5 are thus still valid. The interactions between the atrial and ventricular parts of the DDD pacemaker are well known to the person skilled in the art of pacemakers.

Figure 1E:
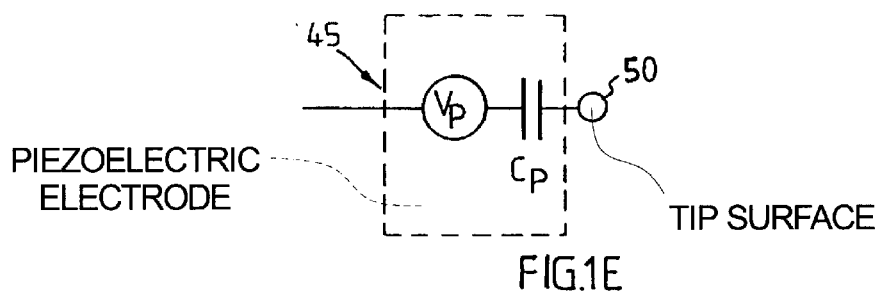
FIG. 1E is a schematic equivalent circuit of the piezoelectric electrode in accordance with an embodiment of the invention.

FIG. 1E shows a schematic equivalent circuit 45 of the electrode in accordance with an embodiment of the invention, whereby the piezoelectric electrode 40, 50 comprises a voltage source $V_p$ and a capacitor $C_p$. The electrode 10 is further characterised by the tip surface 50. The conductor 13, 20 electrically connects the electrode to the electronics of the pacemaker.

A stimulation pulse delivered to the electrode 10 and thus to the piezo electrode 45, will change the thickness of the piezoelectric material during the pulse and two pressure waves will be emitted therefrom, there being one pressure wave for each slope of the stimulation wave. The capacitor $C_p$ of the piezoelectric electrode 40, 50 transmits the electrical stimulation pulse to the heart cells.

Figure 2:
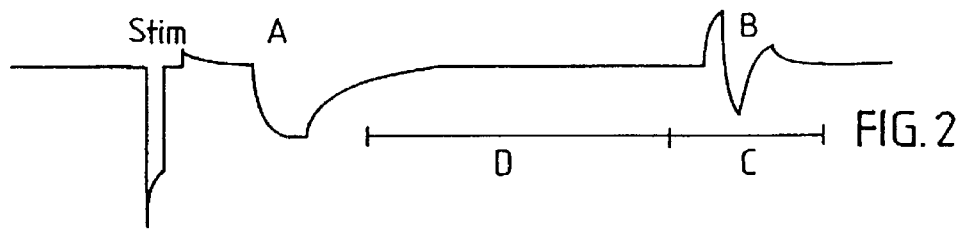
FIG. 2 is a pulse diagram of the detector input signal generated by the electrode in accordance with an embodiment of the invention, and including the stimulation pulse, the electrical evoked response, and the mechanical evoked response.

To avoid charging of the piezoelectric material, the material can be doped or contaminated with a conducting material such as carbon. It is conceivable to have different time constants for the charging. A short time constant, for instance 10–100 ms, entails that the charge has been dissipated before the mechanical response arrives. In this case, only fast events can be monitored/detected (>20 Hz). An alternative is to provide a slow discharge during for instance 1–10 seconds, which prevents a cumulative charge, but which permits a relatively low cut-off frequency fg. If the total resistance against leaking over the piezo-matenal is termed R and the total capacitance is termed R, the following examples can be given:

Example 1, fast tip.
C=10 nF, R=500 kohm=>τ=RC=5 ms=>fg=32 Hz
Example 2, slow tip.
C=100 nF, R=500 Mohm=>τ=RC=0.5 s=>fg=0.32 Hz FIG. 2 shows a pulse diagram of the detector input signal generated by the electrode in accordance with an embodiment of the invention and illustrating the stimulation pulse Stim, the electrical evoked response A and the electrical signal B corresponding to the mechanical evoked response. Consequently, a successful heart stimulation will be sensed as two electrical signals by the detector 110 shown in FIG. 3. First the muscle cells close to the electrode will immediately after the stimulation pulse generate an electrical signal A related to the trigged ion transport. Then the global heart muscle contraction will exert a mechanical pressure on the piezo electrode 45 which generates the second electrical signal B. The electrical signal B arrives within a time window C after a certain time D of the electrical signal A. The time interval D depends on the location of the electrode and on the activity of the autonomic nervous system. However, the time interval D is substantially constant for each individual. The time interval D is approximately 5 to 100 ms if the electrode is located in the ventricle. Furthermore, the electrical signal B appears in a relatively narrow time window C, which is approximately 50 ms if the electrode is located in the ventricle.

A control unit 130, e.g. a microprocessor, includes known means for analyzing the detected electric signals A and B and how they relate to each other and to the stimulation pulse, so that information regarding the condition of the heart can be obtained. This information can therefore be used as a diagnostic tool for analyzing the condition of the heart.

The control unit 130 may obtain information from the dual sensing detector for analyzing the evoked response signals. It is e.g. often difficult to handle fusion beats in pacemakers comprising an autocapture function. A fusion beat is a cardiac depolarization (atrial or ventricular) resulting from two foci. In pacing it typically refers to the ECG waveform which results when an intrinsic depolarization and a pacemaker output pulse occur simultaneously and both contribute to the electrical activation of that chamber. Another difficulty when analyzing evoked response signals is related to the declining electrode polarization after the stimulation pulse. If the polarization artefact is large, compared to the electrical signal generated by the heart, the control unit 130 may interpret the polarization as a capture. A capture occurs when the stimulation results in a heart contraction.

Using this electrode, a new possibility for the control unit 130 to verify capture has been created. If the electrical signal B does not fall within the time interval C, the heart contraction is probably not related to the stimulation pulse. If the electrical signal B arrives before the time window C, a fusion beat is present, or the QRS detector sensitivity is set too low, so that the pacemaker does not inhibit the pacing pulse. If the electrical signal B arrives after the time window C, there is a loss of capture followed by a spontaneously released heart beat.

If only the electrical signal A is present, the detector either senses the polarization artefact due to the sensitivity being too high and should be adjusted, i.e. evoked response oversensing, or the patient has a beat with electromechanical dissociation.

By analyzing the morphology, i.e. duration and amplitude, of the electric signal B, information regarding the heart contractility can be obtained. For patients with coronary artery disease during angina pectoris, the contractile behaviour is changed. With the electrode according to the invention it is possible for the pacemaker to detect this adverse situation and start therapy. The pacing rate should be reduced until the attack is over. This function is especially important for physiologically rate controlled pacemakers such as the ones being controlled by the venous oxygen contents.

Certain patients have a prolonged or varying time between the atrial stimulation A and the atrial evoked electrical response. By letting the control unit 130 start the A-V timer in a two chamber pacing system after the detection of the electrical signal B corresponding to the mechanical evoked response, instead of after the evoked electrical response, these patients will obtain a more stable heart function. The A-V timer is the timer keeping track of the time elapsed between the atrial stimulation A and the ventricular stimulation V.

There are times when the heart in response to a stimulation pulse emits an electrical signal, but does not actually contract (electromechanical dissociation). However, the pacemaker detects and interprets the electrical signal as an evoked response. Since the electrode according to the invention registers both electrical and mechanical evoked response, it can distinguish e.g. hemodynamically stable tachycardias at exercise from a pathological situation. Consequently, the electrode according to the invention is suitable for therapy when using an implantable cardiac defibrillator.

FIG. 3 shows the schematic drawing of a heart pacemaker 100 for tissue stimulation. The heart pacemaker 100 contains a stimulation pulse generator 120 that has its output side connected via a lead 11 to an electrode 10 applied in the ventricle of the heart for delivering stimulation pulses to the heart. Of course, even though FIG. 3 shows the electrode 10 to be located in the ventricle, the invention also covers the electrode 10 being located in the atrium. The stimulation pulse generator 120 can be activated to deliver a stimulation pulse via a control line, which is connected to a corresponding output of a control unit 130, e.g. a microprocessor. The stimulation pulse generated by the stimulation pulse generator 120 may be anyone of the stimulation pulses known to the skilled person. The duration of the each stimulation pulse as well as the amplitude thereof are set by the control unit 130. In the illustrated preferred embodiment, the control unit 130 has access to a memory 140 wherein a program that execute all functions of the heart pacemaker 100 via the control unit 130 is stored. The pacemaker 100 also contains a telemetry unit 150 connected to the control unit 130 for programming and for monitoring the functions of the pacemaker 100 and of parameters acquired therewith on the basis of data exchange with an external programming and monitoring device (not shown).

In order to be able to acquire the reaction of the heart given a stimulation, the pacemaker 100 also contains a detector unit 110 which has an input side connected via the lead 11 to the electrode 10 for acquiring the electrical potential in the heart tissue. This arrangement is simple because only a single electrode 10 is required both for stimulating the heart and for acquiring the reaction thereof Of course, the electrode according to the invention may be used only as stimulation electrode for stimulating tissue or a measuring electrode for acquiring the evoked response for e.g. operating in the VDD stimulating mode. In such cases either the stimulation generator 120 is programmed not to deliver stimulation pulses or the detector unit 110 not to register any evoked response (not shown).

The control unit 130 further contains known means for evaluating the electrical signals received by the detector 110 for making a diagnosis of the condition of the heart depending on e.g. the morphology of the electrical signal B or how the two electrical signals A and B relate to each other and/or to the stimulation pulse, and possibly for starting a therapy based on the made diagnosis.

FIG. 4 shows a schematic circuit diagram of a pacemaker in accordance with a first embodiment of the invention. The stimulation pulse generator includes a charge pump 121, a capacitor $C_1$, e.g. 1 $\mu F$, and a switch SI which, when closed, charges the capacitor to a voltage of e.g. 20 V. When the stimulation pulse generator 120 rapidly transfers charge to the electrode 10, the thickness of the piezoelectric material 50 changes and pressure waves are emitted to the heart tissue. It is known that mechanical irritation of the endocardium can start a heart contraction, the mechanical stimulation may decrease the threshold for the electrical stimulation or may by itself initiate a heart contraction. Because the piezoelectric electrode 40, 50 functions as a capacitor as well, electrical current is transferred to the tissue when closing the switch $S_2$. Since the capacitance $C_p$ of the piezoelectric material preferably is 10 to 100 nF, a relatively high voltage of about 5 to 25 volt is needed during a very short time of about 10 to 100 $\mu s$ for reaching the stimulation threshold. This voltage may be generated inductively or capacitively and then be stored on $C_1$. The voltage is higher than the voltage at conventional electrodes. The total energy used is, however, about the same as with conventional electrodes since the pulse width is small. The detector unit 110 comprising a detector circuit 111 and a charge amplifier 112 detects both electric signals A and B corresponding to the electrical and mechanical evoked response respectively registered by the piezo electrode 45.

An alternative embodiment of the schematic circuit diagram of FIG. 4 is shown in 20 FIG. 5. In order to influence the stimulation threshold, the stimulation pulse generator 120 may generate a stimulation pulse which is chopped with a high frequency of e.g. 10 to 100 kHz. The chopped stimulation frequency may be obtained by opening and closing the switch $S_2$. Due to the chopped stimulation pulse, the piezo sensor generates a series of pressure waves. Since the high frequency improves the electrical transmission through the piezo capacitor $C_p$ more normal pulse amplitudes may be used.

Figure 6:
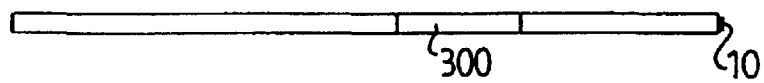
FIG. 6 is a schematic drawing of single lead wherein a piezoelectric electrode in accordance with an embodiment of the invention is placed at the tip of the lead and an intravascular defibrillation electrode is placed behind the piezoelectric electrode.

The piezoelectric electrode 10 may be used together with a defibrillation electrode 300, either as two separated electrodes, i.e. two leads, or in combination on a single lead, whereby the piezoelectric electrode is placed at the tip of the lead and the intravascular defibrillation electrode 300 is placed behind the piezo electrode 10 as is shown in FIG. 6.

Thus an electrode for electrically and mechanically stimulating and detecting evoked response is provided. One skilled in the art will appreciate that the present invention can be practised by other than the described embodiments, which are presented for purposes of illustration and of limitation, and the present invention is limited only by the claims which follow.

What is claimed is:

1. An implantable electrode for an implantable stimulation device, said implantable electrode comprising a piezoelectric electrode having a conductive core covered by biocompatible piezoelectric material adapted for direct contact with tissue when implanted, said piezoelectric material having a piezoelectric surface, with an entirety of said piezoelectric surface being adapted to participate in electrical and mechanical interactions with said tissue, said interactions being selected from the group consisting of electrically and mechanically transferring stimulation energy to said tissue, and electrically and mechanically receiving electrical and mechanical responses of said tissue selected from the group consisting of evoked responses and intrinsic responses.

2. An implantable electrode as claimed in claim 1 wherein said piezoelectric material has a capacitance in a range between 10 and 100 nF.

3. An implantable electrode as claimed in claim 1 wherein said piezoelectric electrode is a tip electrode.

4. An implantable electrode as claimed in claim 3 wherein said piezoelectric electrode is hemispherical.

5. An implantable electrode as claimed in claim 3 wherein said piezoelectric electrode has a planar distal end.

6. An implantable electrode as claimed in claim 1 wherein said piezoelectric electrode is a ring electrode.

7. An implantable electrode as claimed in claim 6 wherein said piezoelectric electrode is coaxial.

8. An electrode lead connectable to an implantable stimulation device, said electrode lead comprising:

a piezoelectric electrode having a conductive core covered by biocompatible piezoelectric material adapted for direct contact with tissue when implanted, said piezoelectric material having a piezoelectric surface, with an entirety of said piezoelectric surface being adapted to participate in electrical and mechanical interactions with said tissue, said interactions being selected from the group consisting of electrically and mechanically transferring stimulation energy to said tissue, and electrically and mechanically receiving electrical and mechanical responses of said tissue selected from the group consisting of evoked responses and intrinsic responses, and a conductor adapted for delivering stimulation energy to said piezoelectric electrode and for conducting electrical signals from said piezoelectric electrode representing said response.

9. An implantable stimulation device for stimulating tissue, comprising:

a piezoelectric electrode having a conductive core covered by biocompatible piezoelectric material adapted for direct contact with tissue when implanted, said piezoelectric material having a piezoelectric surface, with an entirety of said piezoelectric surface being adapted to participate in electrical and mechanical interactions with said tissue, said interactions being selected from the group consisting of electrically and mechanically transferring stimulation energy to said tissue, and electrically and mechanically receiving electrical and mechanical responses of said tissue selected from the group consisting of evoked responses and intrinsic responses, and a conductor adapted for delivering stimulation energy to said piezoelectric electrode and for conducting electrical signals from said piezoelectric electrode representing said response, a stimulation pulse generator connected to said conductor adapted for generating said stimulation energy, and a detector unit connected to said conductor adapted for receiving said signals representing said responses.

10. An implantable stimulation device as claimed in claim 9 further comprising a control unit connected to said detector unit, said control unit being supplied with said signals received by said detector unit and processing said signals.

11. An implantable stimulation device as claimed in claim 10 wherein said control unit includes a fusion beat detector stage for detecting fusion beats in said signals, said fusion beat detector stage determining if said signal arrives before a predetermined time window.

12. An implantable stimulation device as claimed in claim 10 wherein said control unit comprises an analyzing stage for analyzing contractions of a heart by determining a morphology of said signal.

13. An implantable stimulation device as claimed in claim 10 comprising a further electrode connected to said stimulation pulse generator, and wherein said control unit is connected to said stimulation pulse generator and includes an A-V timer for operating said stimulation pulse generator for dual chamber pacing using said piezoelectric electrode and said further electrode, said control unit starting said A-V timer after detection of said signal representing a response.

14. An implantable stimulation device as claimed in claim 10 wherein said control unit includes an electromechanical dissociation detector stage for detecting electromechanical dissociation by determining whether said signal represents both an electrical and a mechanical evoked response of said tissue after emission of said stimulation energy.

15. An implantable stimulation device as claimed in claim 9 wherein said stimulation pulse generator generates said stimulation energy in a chopped stimulation pulse.

16. An implantable stimulation device as claimed in claim 15 wherein said stimulation pulse generator generates said chopped stimulation pulse with a frequency between 10 and 100 kHz.

\* \* \* \* \*